United States Patent
Savidge et al.

(10) Patent No.: US 9,200,015 B2
(45) Date of Patent: Dec. 1, 2015

(54) INOSITOL HEXAKISPHOSPHATE ANALOGS AND USES THEREOF

(71) Applicants: Tor C. Savidge, League City, TX (US); Petril Urvil, Galveston, TX (US); Dhananjaya Nauduri, Galveston, TX (US); Numan Oezguen, Galveston, TX (US); Catherine Schein, Friendswood, TX (US); Werner Braun, Friendswood, TX (US)

(72) Inventors: Tor C. Savidge, League City, TX (US); Petril Urvil, Galveston, TX (US); Dhananjaya Nauduri, Galveston, TX (US); Numan Oezguen, Galveston, TX (US); Catherine Schein, Friendswood, TX (US); Werner Braun, Friendswood, TX (US)

(73) Assignee: The Board of Regents of the University of Texas Systems, Austin, TX (US)

( * ) Notice: Subject to any disclaimer, the term of this patent is extended or adjusted under 35 U.S.C. 154(b) by 0 days.

(21) Appl. No.: 14/052,994

(22) Filed: Oct. 14, 2013

(65) Prior Publication Data
US 2014/0045799 A1    Feb. 13, 2014

Related U.S. Application Data

(62) Division of application No. 13/441,017, filed on Apr. 6, 2012, now abandoned.

(60) Provisional application No. 61/516,639, filed on Apr. 6, 2011.

(51) Int. Cl.
C07F 9/117    (2006.01)
C07F 9/177    (2006.01)
C07F 9/06     (2006.01)
C07F 9/70     (2006.01)

(52) U.S. Cl.
CPC . *C07F 9/117* (2013.01); *C07F 9/06* (2013.01); *C07F 9/177* (2013.01); *C07F 9/70* (2013.01)

(58) Field of Classification Search
CPC ............ C07F 9/117; C07F 9/177; C07F 9/06; C07F 9/70
See application file for complete search history.

(56) References Cited

FOREIGN PATENT DOCUMENTS

WO    WO 88/07047    *    9/1988

OTHER PUBLICATIONS

Kang et al (Antimicrobial Agents and Chemotherapy, Oct. 2011, p. 4850-4857).*
Pruitt et al., 2009, Journal of Biological Chemistry 284(33): 21934-21940.
Author unknown, "Development of Novel Therapeutics for *Clostridial difficile* Infection," Apr. 26, 2013, accessed at: www.its.utmb.edu/mtts/clostridial_difficile_infection.html.
Xu et al., 2005, Tetrahedron Letters 46: 8311-8314.
International Search Report and Written Opinion, PCT/US2012/032469, Jul. 19, 2012.

* cited by examiner

*Primary Examiner* — Melenie McCormick
*Assistant Examiner* — Angela Brown-Pettigrew
(74) *Attorney, Agent, or Firm* — Norton Rose Fulbright US LLP

(57) ABSTRACT

Provided herein are analog and derivative compounds of inositol hexakisphosphate effective to treat a *Clostridium difficile* infection and to neutralize the bacterial toxins produced by the same. In addition, methods of treating the *C. difficile* infection and for neutralizing its toxins with the compounds are provided.

5 Claims, 5 Drawing Sheets

INOSITOL HEXAKISPHOSPHATE ANALOGS AND USES THEREOF

PRIORITY CLAIM

This application is a divisional of and claims priority to U.S. patent application Ser. No. 13/441,017 filed on Apr. 6, 2012, which claims priority to U.S. Provisional Patent Application Ser. No. 61/516,639 filed Apr. 6, 2011, which is incorporated herein by reference in its entirety.

STATEMENT REGARDING FEDERALLY FUNDED RESEARCH

This invention was made with government support under 1UL1RR029876-01 and DK078032-01 awarded by the John S. Dunn Gulf Coast Consortium for Chemical Genomics Robert A. Welch Collaborative Grant Program and NIDDK, respectively. The government has certain rights in the invention.

BACKGROUND

I. Field of the Invention

The present invention relates generally to microbiology, pharmaceutical chemistry and antibiotic formulations. More specifically, the present invention relates to inositol hexakisphosphate analogs.

II. Description of the Related Art

*Clostridium difficile* is a Gram-positive, spore-forming anaerobic bacillus that is a common cause of nosocomial antibiotic-associated diarrhea and is the etiologic agent of pseudomembranous colitis. The disease ranges from mild diarrhea to life threatening fulminating colitis. Antibiotic use in patients results in a reduction of the commensal gut microflora. *C. difficile* is resistant to most antibiotics, which gives it a competitive advantage over normal bacterial flora resulting in its proliferation and toxin production.

*C. difficile* enterotoxins (TcdA and TcdB) are the major cause of the disease since toxin-deficient strains are avirulent. Standard therapy depends on treatment with vancomycin or metronidazole, neither of which is fully effective. Moreover, up to 35% of patients infected with *C. difficile* relapse following treatment. The primary treatment option for recurrent *C. difficile* infection (CDI) is still metronidazole or vancomycin. *C. difficile* infection accounts for approximately 25% of cases of antibiotic-associated diarrhea and the incidence of infection is rising steadily in North America, with yearly costs in the U.S. estimated at $3.2 billion. Several recent hospital outbreaks of *C. difficile* infection associated with high morbidity and mortality rates have been attributed to the widespread use of broad-spectrum antibiotics. The emergence of new and more virulent *C. difficile* strains also contributes to the increased incidence and severity of the disease. Because of the steadily rising incidence and severity, *C. difficile* infection is an important emerging drug-resistance associated disease.

The incidence of *C. difficile* carriage in healthy adults is around 3-5%. By contrast, in hospitalized adults taking antibiotics, the rate of colonization increases substantially to 20-40%, and is associated with a high disease burden. According to the U.S. Agency of Healthcare Research and Quality (AHRQ), the prevalence of hospital patients infected with *C. difficile* jumped 200% from 2000 to 2005, which follows a 74% increase from 1993 to 2000. This rapid increase in *C. difficile* infection cases is attributed to the use of broad-spectrum antibiotics and/or the emergence of new hypervirulent *C. difficile* strains, such as BI/NAP1/027.

*C. difficile* infection is associated with a wide spectrum of clinical outcomes ranging from asymptomatic carriage to fulminant and fatal colitis. Severe *C. difficile* infection may also be associated with systemic manifestations including marked leukocytosis, hypotension, renal failure, respiratory failure, coagulopathy, and lactic acidosis. Refractory cases, not responding to vancomycin and/or metronidazole treatment is not uncommon. A recent study found that 22.1% of hospital in-patients with *C. difficile* infection had severe disease. The incidence of in-hospital deaths in the cohort of patients with *C. difficile* infection was 12.1%, and mortality caused primarily by *C. difficile* infection was 4.0%. Surgical intervention in the form of sub-total colectomy can be life-saving in severe, fulminant, or refractory *C. difficile* infection. However, patients with severe *C. difficile* infection are typically elderly, critically ill, and are at high risk for surgical and anesthetic complications.

Several reports have described clinical improvement following use of passive antitoxin immunotherapy with normal pooled intravenous immunoglobulin to avoid surgery and prevent death. More recently, passive immunotherapy using human IgG monoclonal antitoxins was reported to be effective in preventing recurrent *C. difficile* infection. However, it did not confer protection against toxin activity, and the length of hospitalization was not significantly reduced. Other options, such as probiotics and anion-exchange resins, have limited efficacy and are potentially harmful. Complementary therapy is therefore urgently warranted to neutralize toxin activity. Experimental therapy currently under clinical development includes toxin-absorbing polymers and new antibiotics.

There is a recognized need in the art for alternative therapies for Clostridium difficile infections. The present invention fulfills this long-standing need and desire in the art by providing inositol hexakisphosphate-based compounds effective to treat *C. difficile* infections and to neutralize its toxins.

SUMMARY

The present invention is directed to an inositol hexakisphosphate analog compound. In certain aspects, an inositol hexakisphosphate analog will be an allosteric activator or inhibitor of *C. difficile* exotoxin cleavage. In further aspects, the analog will be a degradation resistant (e.g., phytase resistant) allosteric activator of *C. difficile* exotoxin cleavage. In certain embodiments the derivative or analog compound has a chemical structure of Formula I Formula I $$\text{R}_3\text{O} \underset{\underset{\text{OR}_5}{|}}{\overset{\overset{\text{OR}_2}{|}}{\diagdown}} \text{OR}_1$$
$$\text{R}_4\text{O} \diagup \qquad \diagdown \text{OR}_6$$

where $R_1$-$R_6$ independently are —PO(OH)$_2$, —PS(OH)$_2$, —PSe(OH)$_2$, —AsO$_3$, or NO associated with —PO(OH)$_2$ (i.e., —PO(OH)$_2$NO), whereby at least one of $R_1$-$R_6$ is —PS(OH)$_2$, —PSe(OH)$_2$, or NO associated with —PO(OH)$_2$ (i.e., PO(OH)$_2$NO). In certain aspects $R_1$ and $R_3$ are not both —$PSe(OH)_2$ or —$PS(OH)_2$ when $R_2$, $R_4$, $R_5$, $R_6$ are —$PO(OH)_2$. In certain aspects, $R_1$ is not —$PS(OH)_2$ or —$PSe(OH)_2$ if $R_2$-$R_6$ are —$PO(OH)_2$. In further aspects, the analog can be a pharmacologically effective salt of the compounds described herein. In other aspects, the analog can be a derivative, such as the pyrophosphates IP7 and IP8.

Certain embodiments are directed to inositol analogs having the chemical formula of Formula I. In certain embodiments the inositol analog is a myo-inositol analog. In further aspects, the inositol analog is a neo-inositol analog. In still further aspects, the inositol analog is a D-chiro-inositol analog. In further aspects, the inositol analog is a L-chiro-inositol analog. In certain aspects, the inositol analog is a muco-inositol analog. In still further aspects, the inositol analog is an allo-inositol analog. In still further aspects, the inositol analog is a scyllo-inositol analog. In yet further aspects, the inositol analog is an epi-inositol analog. In certain aspects, the inositol analog is a cis-inositol analog.

As used herein, "analog" refers to a chemical compound that is structurally similar to a parent compound, but differs in composition (e.g., differs by appended functional groups or substitutions). The analog may or may not have different chemical or physical properties than the original compound and may or may not have improved biological and/or chemical activity. For example, the analog may be more hydrophilic or it may have altered reactivity as compared to the parent compound. The analog may mimic the chemical and/or biologically activity of the parent compound (i.e., it may have similar or identical activity), or, in some cases, may have increased or decreased activity.

The present invention is directed to an inositol hexakisphosphate analog compound. The analog compound has a chemical structure of Formula I wherein $R_1$ is —$PSe(OH)_2$ and (i) $R_2$-$R_6$ (i.e., $R_2$, $R_3$, $R_4$, $R_5$, and $R_6$) are —$PO(OH)_2$ or (ii) $R_2$-$R_6$ are independently —$PO(OH)_2$, —$PS(OH)_2$, —$PSe(OH)_2$, —$AsO_3$, or $PO(OH)_2NO$, but not all are —$PO(OH)_2$. In certain aspects, $R_2$ is —$PSe(OH)_2$, and $R_1$ and $R_3$-$R_6$ are —$PO(OH)_2$. In further aspects, $R_4$ is —$PSe(OH)_2$, and $R_1$-$R_3$ and $R_5$-$R_6$ are —$PO(OH)_2$. In still further aspects, $R_5$ is —$PSe(OH)_2$, and $R_1$-$R_4$ and $R_6$ are —$PO(OH)_2$. In certain aspects, $R_1$-$R_4$ are —$PSe(OH)_2$ and $R_5$-$R_6$ are —$PO(OH)_2$. In certain aspects, one or more of the —$PO(OH)_2$ groups is further modified to a —$PO(OH)_2NO$. The NO group can be covalently or non-covalently bound to the analog. In a further aspect, the compound is a pharmacologically effective salt or derivative of these compounds.

In certain aspects, the derivative or analog compound has a chemical structure of Formula I where $R_1$ is —$PS(OH)_2$ and $R_2$-$R_6$ are —$PO(OH)_2$. In further aspects, $R_2$ is —$PS(OH)_2$ and $R_1$ and $R_3$-$R_6$ are —$PO(OH)_2$. In still further aspects, $R_4$ is —$PS(OH)_2$ and $R_1$-$R_3$ and $R_5$-$R_6$ are —$PO(OH)_2$. In certain aspects, $R_1$, $R_5$, and $R_3$ are —$PS(OH)_2$, and $R_2$ and $R_4$-$R_6$ are —$PO(OH)_2$. In further aspects, R5 is —$PS(OH)_2$ and $R_1$-$R_4$ and $R_6$ are —$PO(OH)_2$. In still further aspects, $R_1$-$R_4$ are —$PS(OH)_2$ and R5-R6 are —$PO(OH)_2$. In certain aspects the analog is an inhibitor of exotoxin cleavage. In certain aspects, the compounds are pharmacologically effective salt or derivative of these compounds.

In a further aspect, the derivative or analog compound has a chemical structure of Formula I where $R_1$-$R_6$ independently are —$PO(OH)_2$ or —PO(OH)2NO (NO associated covalently or ionically with —$PO(OH)_2$), whereby at least one of $R_1$-$R_6$ is NO associated with —$PO(OH)_2$, or a pharmacologically effective salt or derivative thereof.

In certain embodiments an inositol analog has a chemical structure of formula I where $R_1$, $R_2$, $R_3$, $R_4$, $R_5$, and $R_6$ are independently —$PS(OH)_2$, —$PSe(OH)_2$, —$AsO_3$, or —$PO(OH)NO$. In certain aspects, $R_1$, $R_2$, $R_3$, $R_4$, $R_5$, and $R_6$ are —$PS(OH)_2$. In certain aspects, $R_1$, $R_2$, $R_3$, $R_4$, $R_5$, and $R_6$ are —$PSe(OH)_2$. In certain aspects, $R_1$, $R_2$, $R_3$, $R_4$, $R_5$, and $R_6$ are —$AsO_3$. In certain aspects, $R_1$, $R_2$, $R_3$, $R_4$, $R_5$, and $R_6$ are —$PO(OH)_2NO$. In certain aspects, $R_1$, $R_2$, and 1, 2, 3, or 4 of $R_3$, $R_4$, $R_5$, and $R_6$ are —$PS(OH)_2$, —$PSe(OH)_2$, —$AsO_3$, or —$PO(OH)_2NO$. In further aspects $R_1$, $R_4$, and 1, 2, 3, or 4 of $R_2$, $R_3$, $R_5$, and $R_6$ are —$PS(OH)_2$, —$PSe(OH)_2$, —$AsO_3$, or —$PO(OH)NO$. In still further aspects, $R_1$, $R_5$, and 1, 2, 3, or 4 of $R_2$, $R_3$, $R_4$, and $R_6$ are —$PS(OH)_2$, —$PSe(OH)_2$, —$AsO_3$, or —$PO(OH)NO$. In certain aspects, $R_1$, $R_6$, and 1, 2, 3, or 4 of $R_2$, $R_3$, $R_4$, and $R_5$ are —$PS(OH)_2$, —$PSe(OH)_2$, —$AsO_3$, or —$PO(OH)NO$. In certain embodiments the inositol analog is a myo-inositol analog.

The present invention also is directed to a method for neutralizing a pathogenic *Clostridium difficile* bacteria toxin. The method comprises contacting the *C. difficile* bacteria or toxin with the compounds described herein, where the compound potentiates or inhibits cysteine-dependent toxin self-cleavage, thereby neutralizing the same.

The present invention is directed further to a method of treating a pathogenic *Clostridium difficile* infection in a subject. The method comprises administering to the subject a pharmacologically effective dose of the compounds described herein.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "contacting" refers to any suitable method of bringing the analog and derivative compounds of inositol hexakisphosphate into contact with a *Clostridium difficile* toxin or the bacterial cell comprising the same. In vitro or ex vivo this is achieved by exposing the compound to the toxin and/or *C. difficile* bacteria in a suitable medium. For in vivo applications, any known method of administration is suitable as described herein.

As used herein, the term "subject" refers to any recipient of the novel compounds or a pharmaceutical composition thereof provided herein that are effective as therapeutics or inhibitors against a *Clostridium difficile* infection.

Other and further aspects, features, and advantages of the present invention will be apparent from the following description of the presently preferred embodiments of the invention. These embodiments are given for the purpose of disclosure.

DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIG. 1 shows CPD domain boundaries in TcdB.

FIGS. 2A-2B shows the Toxin InsP$_6$ sensor. FIG. 2A shows InsP$_6$-induced toxin cleavage and the allosteric sensor activity of the glutamic acid (E743) residue. Enhanced InsP$_6$-induced self-cleavage is evident in the toxin E743A mutant, whereas no cleavage is evident in the inactive catalytic cysteine (C698S) mutant. FIG. 2B shows that, using an N-terminus specific anti-TcdB antibody, it is demonstrated that toxin cleavage is approximately 2-orders of magnitude more sensitive following genetic disruption of the toxin allosteric-sensor mechanism (E743A).

FIGS. 3A-3D show therapeutic allostery and examples of the assays to test designed compounds. FIG. 3A shows that InsP$_6$-autocleaves (left) and inhibits toxin-induced cytotoxicity (right) in Caco-2 colonocytes (AC$_{50}$ and IC$_{50}$=10 µM). Toxin (TcdB) cleavage fragments are shown in FIG. 3B, and are absent in the presence of a CPD inhibitor. (FIGS. 3C-3D) Kaplan-Meier survival plots of infected mice. C57BL/6 mice were inoculated with $10^6$ C. difficile. Oral InsP$_6$ (but not inositol) therapy dose dependently protects mice from CDI (0.25 and 2.5 mg/kg/day delivered intragastrically; n=12/group, survival at day 6). The protective effect is statistically significant in the 2.5 mg/kg group, which is within the daily recommended dose for humans.

FIGS. 4A-4B show Nitroso-InsP$_6$ experimental UV spectra (FIG. 4A) and LC-MS for nitroso-InsP$_6$ vs. InsP$_6$ (FIG. 4B).

FIGS. 5A-5B shows that Nitroso-InsP$_6$ shows greater amelioration in experimental CDI. FIG. 5A shows antimicrobial activity of InsP$_6$ vs. InsP$_6$-NO against C. difficile. FIG. 5B demonstrates how mini-osmotic pumps (7 day pumps; n=10/group) were surgically implanted to deliver inositol derivatives at 12.5 mg/kg/day, starting 1 day prior to C. difficile inoculation ($10^6$ bacteria). In this set of experiments, vehicle treatment was associated with 100% mortality, vs. 40% and 10% for InsP$_6$ and nitroso-InsP$_6$ groups, respectively.

DESCRIPTION

Figure 1:
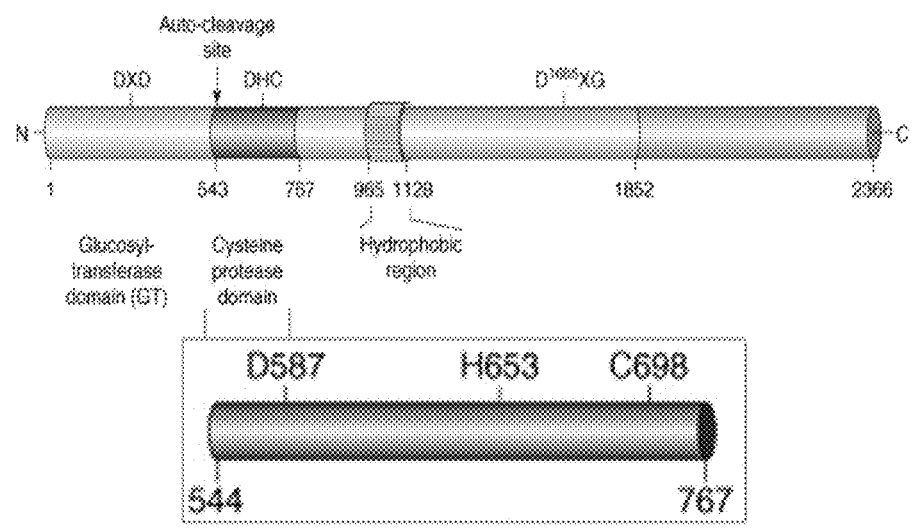

C. difficile infection is a toxin-mediated disease. Two exotoxins, toxin A (TcdA) and toxin B (TcdB), are the major virulence factors. C. difficile strains that lack both toxin genes are non-pathogenic. TcdA and TcdB are structurally similar to each other. Both toxins consist of at least three functional domains that are now well defined. The C-terminus receptor binding domain (RBD) has a α-solenoid structure and is involved in receptor binding. The middle part is involved in translocation of the toxins into the target cells, and the N-terminus is a catalytic glucosyltransferase (GT) domain. Interactions between the C-terminal receptor binding domain and host cell receptors initiate receptor-mediated endocytosis. Although the precise intracellular mode of action remains unclear, the toxins undergo a conformational change at the low pH of the endosomal compartment, leading to a membrane insertion and channel formation. An essential host-derived virulence cofactor inositol hexakisphosphate (InsP$_6$) is then required to trigger an allosteric structural change that activates a cysteine protease domain to induce toxin self-cleavage, resulting in the release of the GT-effector domain into the cytosol. Once in the cytosol, the catalytic GT-domain mono-O glucosylates small GTPases of the Rho family, including RhoA, Rac1, and Cdc42. Glucosylation of Rho proteins inhibits their "molecular switch" function, thus blocking Rho GTPase-dependent signaling in intestinal epithelial cells, leading to alterations in the actin cytoskeleton, massive fluid secretion, acute inflammation and necrosis of the colonic mucosa.

Cysteine-dependent cleavage is a crucial activation mechanism for TcdA and TcdB because it facilitates toxin entry into cells. Specific inhibition of this cleavage reaction significantly attenuates the toxin. This virulence mechanism is dependent on cellular InsP$_6$ that activates the cysteine protease domain (CPD) to facilitate toxin self-cleavage. Cysteine protease domain crystal structures for TcdA and the closely aligned Vibrio cholerae RTX toxin demonstrate a well defined catalytic cleft separated from a positively charged InsP$_6$-binding pocket abutting a flexible β-hairpin fold (β-flap).

In one embodiment of the present invention there is provided an inositol hexakisphosphate analog or derivative compound having a chemical structure:

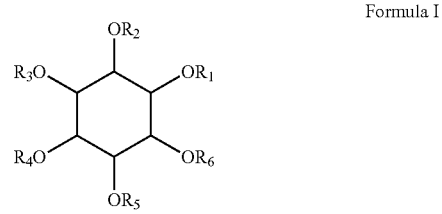

Formula I where R1-R6 independently are —PO(OH)$_2$, —PS(OH)$_2$, —PSe(OH)$_2$, —AsO$_3$, or NO associated with —PO(OH)$_2$, whereby at least one of R$_1$-R$_6$ is —PS(OH)$_2$, —PSe(OH)$_2$, or NO associated with —PO(OH)$_2$, and R1 and R3 are not both —PSe(OH)$_2$; or a pharmacologically effective salt or derivative thereof. In certain aspects, R$_1$ is —PS(OH)$_2$ or —PSe(OH)$_2$ when R$_2$-R$_6$ are not —PO(OH)$_2$. In all embodiments and aspects the inositol hexakisphosphate analog or derivative compound may comprise a pharmaceutical composition with a pharmaceutically acceptable carrier.

In one aspect R$_1$ may be —PS(OH)$_2$ and R$_2$-R$_6$ may be —PO(OH)$_2$. In one aspect R$_1$ may be —PS(OH)$_2$ and one or more of R$_2$-R$_6$, but not all of R$_2$-R$_6$ is —PO(OH)$_2$. In another aspect R$_2$ may be —PS(OH)$_2$, and R$_1$ and R$_3$-R$_6$ may be —PO(OH)$_2$. In yet another aspect R$_4$ may be —PS(OH)$_2$ and R$_1$-R$_3$ and R$_5$-R$_6$ may be —PO(OH)$_2$. In yet another aspect of this embodiment R$_5$ may be —PS(OH)$_2$ and R$_1$-R$_4$ and R$_6$ may be —PO(OH)$_2$. In yet another aspect R$_1$ and R$_3$ may be PS(OH)$_2$, and R$_2$ and R$_4$-R$_6$ may be —PO(OH)$_2$. In yet another aspect R$_1$-R$_4$ may be —PS(OH)$_2$ and R$_5$-R$_6$ may be —PO(OH)$_2$. In yet another aspect R$_1$ may be —PSe(OH)$_2$ and R$_2$-R$_6$ may be —PO(OH)$_2$. In yet another aspect R$_1$ may be —PSe(OH)$_2$ and one or more, but not all, of R$_2$-R$_6$ may be —PO(OH)$_2$. In yet another aspect R$_2$ may be —PSe(OH)$_2$, and R$_1$ and R$_3$-R$_6$ may be —PO(OH)$_2$. In yet another aspect R4 may be —PSe(OH)$_2$ and R$_1$-R$_3$ and R$_5$-R$_6$ may be —PO(OH)$_2$. In yet another aspect R$_5$ may be —PSe(OH)$_2$, and R$_1$-R$_4$ and R$_6$ may be —PO(OH)$_2$. In yet another aspect R$_1$-R$_4$ may be —PSe(OH)$_2$ and R$_5$-R$_6$ may be —PO(OH)$_2$. In yet another aspect of this embodiment the NO substituent may be associated covalently or ionically with —PO(OH)$_2$.

In a related embodiment, there is provided an inositol hexakisphosphate analog or derivative compound having a chemical structure as described supra where R$_1$ is —PSe(OH)$_2$ and R$_2$-R$_6$ are —PO(OH)$_2$; R$_2$ is —PSe(OH)$_2$, and R1 and R$_3$-R$_6$ are —PO(OH)$_2$; R$_4$ is —PSe(OH)$_2$ and R$_1$-R$_3$ and R$_5$-R$_6$ are —PO(OH)2; R$_5$ is —PSe(OH)$_2$ and R$_1$-R$_4$ and R$_6$ are —PO(OH)$_2$; or R$_1$-R$_4$ are —PSe(OH)$_2$ and R$_5$-R$_6$ are —PO(OH)$_2$; a pharmacologically effective salt or derivative thereof.

In another related embodiment there is provided an inositol hexakisphosphate analog or derivative compound having a chemical structure as described supra where R$_1$ is —PS(OH)$_2$ and R$_2$-R$_6$ are —PO(OH)$_2$; R$_2$ is —PS(OH)$_2$, and R$_1$ and R$_3$-R$_6$ are —PO(OH)$_2$; R$_4$ is —PS(OH)$_2$ and R$_1$-R$_3$ and R$_5$-R$_6$ are —PO(OH)$_2$; R$_5$ is —PS(OH)$_2$, and R$_1$-R$_4$ and R$_6$ are —PO(OH)$_2$; R$_1$ and R$_3$ are —PS(OH)$_2$, and R$_2$ and R$_5$-R$_6$ are —PO(OH)$_2$; R$_1$-R$_4$ are —PS(OH)$_2$ and R$_5$-R$_6$ are —PO(OH)$_2$ or a pharmacologically effective salt or derivative thereof.

In another related embodiment there is provided an inositol hexakisphosphate analog or derivative compound having a chemical structure as described supra where R$_1$-R$_6$ independently are —PO(OH)$_2$ or —PO(OH)NO (NO associated covalently or ionically with —PO(OH)$_2$), whereby at least one of R$_1$-R$_6$ is —PO(OH)$_2$NO; or a pharmacologically effective salt or derivative thereof.

In another embodiment of the present invention there is provided a method for neutralizing a toxin in a pathogenic *Clostridium difficile* bacteria, comprising contacting the *C. difficile* bacteria with a compound as described supra, wherein said compound inhibits cysteine-dependent toxin self-cleavage, thereby neutralizing the same. In this embodiment the toxin may be one or both of TcdA or TcdB.

In yet another embodiment of the present invention, there is provided a method for treating a pathogenic *Clostridium difficile* infection in a subject, comprising administering to the subject a pharmacologically effective dose of the compound as described supra. In certain embodiment the compound may be comprised an oral formulation and/or administered orally.

In yet another embodiment of the present invention there is provided a method for identifying an inositol hexakisphosphate analog or derivative compound effective to inhibit self-cleavage of a pathogenic *Clostridium difficile* toxin, comprising designing a 3D-pharmacophore, at least in part in silica, based on a crystal structure of inositol hexakisphosphate bound to the toxin; selecting a potential inhibitor compound; and analyzing a structure activity relationship of the potential inhibitor with the toxin 3D-pharmacophore to determine inhibitory activity of toxin self-cleavage, thereby identifying an inhibitory inositol hexakisphosphate analog or derivative compound. Further to this embodiment the method may comprise optimizing the structure of the inhibitory inositol hexakisphosphate analog or derivative compound.

In a related embodiment, there is provided a 3D-pharmacophore based on the crystal structure of inositol hexakisphosphate bound to the *C. difficile* toxin as described supra.

In another related embodiment, there is provided an inositol hexakisphosphate analog or derivative compound or a pharmaceutical composition thereof identified by the method described supra.

Provided herein are analog and derivative compounds of inositol hexakisphosphate that demonstrate therapeutic activity against pathogenic *Clostridium difficile* and neutralize its toxins. In certain aspects the inositol-hexakisphosphate is myo-inositol (1R,2R,3S,4S,5R,6S)-cyclohexane-1,2,3,4,5,6-hexayl hexakis [dihydrogen (phosphate)] (myo-InsP$_6$). Particularly, the derivative and analog compounds are effective to neutralize the toxins that are produced by pathogenic *C. difficile*. Preferably, the compounds described herein are effective to inhibit self-cleavage of a pathogenic *Clostridium difficile* toxin TcdA and TcdB. It is contemplated that the therapeutic effect is at least in part due to toxin neutralization.

Generally, the novel derivative and analog compounds are substituted at one or more of the P1-P6 phosphate moieties substituted at C1-C6, respectively, comprising the cyclohexane ring. Particularly, P1, P2, P4, or P5; P1-P4; or P1 and P3 phosphates may contain a sulfur or P1, P2, P4, or P5; or P1-P4 may contain selenium or arsenic. Alternatively, at least one of P1-P6 may be associated with a nitroso moiety either covalently or ionically. The compounds presented herein may be synthesized by known and standard chemical synthetic methods, for example see Xu et al., Tetrahedron Letters 46:8311-14, 2005; Zhang et al., Bioorganic and Medicinal Chemistry Letters 18:762-66, 2008, both of which are incorporated herein by reference in their entirety.

It is contemplated that potential inhibitor compounds may be designed utilizing a 3D-pharmacophore based on a crystal structure of a *C. difficile* toxin, for example, TcdA or TcdB, containing inositol hexakisphosphate or other similar compound bound therein using at least in part computer aided design as is known in the art. A potential inhibitor is selected and a structure activity relationship is analyzed by well-known and standard assays. Potential compounds may be derived from the derivative and analog compounds described herein, may be designed at least in part using known in silica methods, may be selected from a chemical library or may be derivative or analogs of the same, or may be synthesized de novo. A potential compound that is determined to potentiate or inhibit self-cleavage of a pathogenic *Clostridium difficile* toxin is suitable for the therapeutic and/or inhibitory methods provided. In addition, such recognized compounds may be further optimized structurally to increase therapeutic and inhibitory efficacy.

Thus, the present invention provides methods for neutralizing a Clostridium difficile toxin either in vitro or in vivo. For example, the bacteria or the toxins may be contacted by one or more of the compounds described herein in vitro. Effectiveness may be determined by an assay to determine if the toxin cleavage product is present as is known in the art.

As such, the present invention also provides methods for treating a Clostridium difficile infection in a subject. The derivative and analog compounds provided may be administered one or more times to a subject in need of such treatment. Dosage formulations of the inositol hexakisphosphate derivatives and analogs may comprise conventional non-toxic, physiologically or pharmaceutically acceptable carriers or vehicles suitable for the method of administration. These compounds or pharmaceutical compositions thereof may be administered independently one or more times to achieve, maintain or improve upon a pharmacologic or therapeutic effect derived from these compounds or other agents suitable for *C. difficile* infection being treated. It is well within the skill of an artisan to determine dosage or whether a suitable dosage comprises a single administered dose or multiple administered doses. An appropriate dosage depends on the subject's health, the progression or remission or at risk status of the infection, the route of administration and the formulation used. Preferably, these compounds may be administered in an oral formulation, although the scope of the invention does not limit administration to an oral route.

EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Allosteric Activation of TcdA and TcdB Autocleavage

In order to better understand how $InsP_6$ allosterically activates TcdA and TcdB autocleavage, cysteine protease domain homology models were generated that included the uncut N-terminus substrate cleavage fragment within the P1-substrate residue catalytic cleft (FIG. 1). These studies have identified a reaction mechanism in response to conformational-coupling by $InsP_6$. Analysis of these N-terminus extended cysteine protease domain models demonstrated an extensive network of interconnecting hydrogen bonds within the catalytic active site. Because of the unusually large distances (>6 Å) between the catalytic cysteine and histidine in all of the microbial cysteine protease domain crystal structures, the histidine residue appears to play a role in substrate orientation within the P1 pocket rather than conferring nucleophilicity to the catalytic cysteine thiolate as conventionally happens in cysteine proteases. The aspartic acid may stabilize the histidine imidazolium ring, and hydrogen bonding between a novel glutamic acid residue and the catalytic cysteine modulates thiolate reactivity. Thus, this tetrad active site motif appears to have developed an allosteric sensor mechanism (achieved via hydrogen bonding between a highly conserved glutamic acid (Glu) and the catalytic cysteine) in order to restrict toxin self-cleavage to situational exposure to $InsP_6$ cofactor. Applicants note that their analysis is not to be construed as a limitation on the claimed subject matter unless expressly included as a limitation.

Figures 2A, 2B:
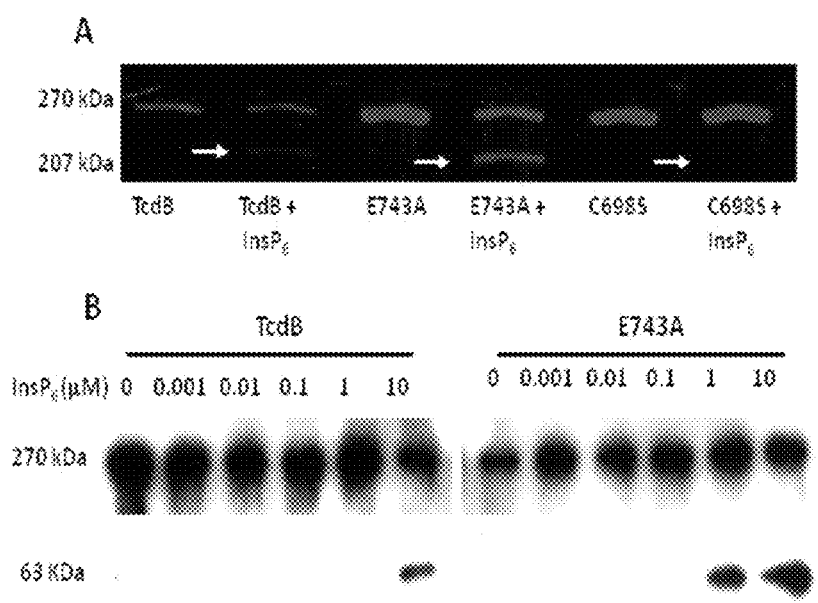

This catalytic tetrad function is demonstrated experimentally by site-directed mutagenesis in TcdB, where there was generated (i) a catalytically dead Cys698Ser mutation; (ii) a highly attenuated toxin His655Ala mutation ($10^4$ fold inhibition), and (iii) an enhancing Glu743Ala mutation, which sensitizes toxin self-cleavage into the nM $InsP_6$ range (a concentration that is readily achieved in the gut lumen by dietary $InsP_6$) (FIGS. 2A-2B). Further, this regulatory glutamic acid is located on the flexible cysteine protease domain β-flap, a structure likely to be regulated by $InsP_6$. However, because of the instability of the cysteine protease domain in the absence of $InsP_6$ cofactor, it has not been possible to generate crystal structures of the native unbound configuration to elucidate this β-flap mechanism. Therefore, in order to better understand the structural basis for the $InsP_6$ allostery, molecular dynamics (MD) structural simulations of $InsP_6$ binding to the cysteine protease domain of TcdA, TcdB, and *V. cholerae* RTX toxin were performed.

$InsP_6$ binds to a highly conserved positively charged binding pocket that conforms to the edge of the flexible allosteric β-flap. The molecular dynamics-simulation models consistently showed that allosteric $InsP_6$ binding facilitates substrate access to the active site cysteine in the catalytic groove by inducing conformational changes that leverage the flexible β-flap away from catalytic cleft. Moreover, $InsP_6$ re-orientates the glutamic acid side chain relative to the catalytic cysteine. Thus, $InsP_6$ allostery appears to facilitate toxin self-cleavage by promoting accessibility and reactivity of the active site cysteine thiolate for the cleavage substrate.

Extracellular $InsP_6$ concentrations in blood and plasma are generally too low (<1 nM) to facilitate autocleavage of the *C. difficile* toxins. However, in the gut lumen $InsP_6$ can reach much higher concentrations from dietary sources, although it seems unlikely that sufficiently high levels are achieved to neutralize the toxins because gut-associated enzymes rapidly degrade $InsP_6$ to inactive myo-inositol ((1R,2R,3S,4S,5R,6S)-cyclohexane-1,2,3,4,5,6-hexol)) and inorganic phosphate. Phytic acid ($InsP_6$) is the principle storage form of phosphorous in many plant tissues, especially in the fiber of bran and seeds. Because $InsP_6$ is currently regarded as the main chemoprotective agent in dietary fiber due to its potent anti-oxidant and metal ion chelator properties, it is available to the public as a nutritional supplement. The enzyme meso-inositol hexaphosphate phosphohydrolase (phytase) actively degrades $InsP_6$ into lower inositol phosphate derivatives, rapidly reducing its bioavailability in the colon.

Three classes of phytase enzymes exist which initiate dephosphorylation of $InsP_6$ at different positions on the inositol ring, and provide different isomers of lower inositol phosphates. These phytase families have pronounced stereospecificity targeting the P3, P5, and/or P4/6 positions, and have a strong preference for equatorial over axial phosphate groups. Because the lower inositol phosphate products are poor allosteric activators of the toxin cysteine protease, the present invention generates non-hydrolysable phytase-resistant $InsP_6$ analogs that remain potent toxin inhibitors in the colon. Echelon Biosciences has generated stable racemic P1/3 phosphoroselenium and phosphorothiolate $InsP_6$ derivatives that are resistant to the P3 family of microbial phytases, which represents the major enzyme class in the human colon. Computational 3D-pharmacophores and structure activity relationship analysis of the toxin allosteric binding site will aid in the optimization of these phytase-resistant $InsP_6$ derivatives for therapy.

*C. difficile*, newly emerged in its present drug resistant hyper-virulent form, causes serious and potentially fatal inflammation of the colon. Currently, there is an urgent need to find alternative therapy for CDI as *C. difficile* is rapidly developing resistance to antibiotic treatment. Although an antitoxin vaccine program is in clinical trials, the efficacy of this approach remains highly uncertain and problematic since patients with severe CDI typically tend to be the elderly and the critically ill. Passive systemic antitoxin immunotherapy has been reported to be effective in preventing disease recurrence in CDI patients, but failed to confer significant clinical benefits or reduce the length of hospitalization. Oral adaptation of passive immunotherapy is not feasible or economical. Probiotics and anion-exchange resins remain unproven treatment options for CDI with limited efficacy. Thus, in CDI, there is an urgent need to develop therapeutics not subject to antimicrobial resistance. A goal of the present invention is to address these critical issues by developing antimicrobial inositol phosphate-based therapy that also neutralizes toxin activity in the colon.

Cysteine proteases degrade polypeptides via a common catalytic mechanism that normally involves a nucleophilic cysteine thiol in a catalytic triad. This important enzyme class regulates many cellular activities in eukaryotic cells and in infectious pathogens, including *C. difficile*. Thus, various strategies are being explored to combat infectious disease by specific inhibition of microbial cysteine proteases. Proof-of-concept for such an approach has been provided by demonstrating that wide-spectrum cysteine protease inhibitors suppress both viral and parasitic disease. Vinyl sulfone-based peptides are efficient inhibitors of microbial cysteine proteases, such as cruzain and falcipains, by forming irreversible covalent bonds with the thiolate of the catalytic cysteine.

Although such irreversible inhibitors are quite potent, with $IC_{50}$ values in the nanomolar range, the poor selectivity for parasitic over human cysteine proteases remains a significant concern. Also, it is desirable to design non-peptide based reversible inhibitors to minimize the potential toxicity that can be observed with irreversible inhibitors.

With the recent discovery that *C. difficile* toxins require cysteine protease activity for virulence, specific targeting of this enzyme class represents an important therapeutic strategy in combating CDI. The present invention designs small molecule therapeutics to combat CDI that mimics the cytosolic allosteric cofactor, inositol hexakisphosphate ($InsP_6$) of these toxins. As the exotoxin cysteine protease active site self-processes the toxin to an active state, is normally inaccessible to inhibitors. In certain embodiments the $InsP_6$ analog is designed to trigger the accessible and highly conserved allosteric site, inducing autolytic cleavage and preventing the toxins from entering mammalian cells. This approach has been validated by showing that high levels of dietary $InsP_6$ can mitigate CDI in an animal model. However, oral $InsP_6$ therapy may be limited due to enzymatic degradation by gut phytases. Thus, the present invention develops new degradation resistant or phytase-resistant inositol analogs that bind to the allosteric site and rapidly trigger the autolysis while the toxin is still in the extracellular milieu. Computational modeling of the toxin-$InsP_6$ allosteric mechanism and structure-based design of the allosteric binding site assist in the design and selection of inhibitors. Data for structure-activity relationship analysis is generated for phosphoroseleno-, phosphorothiolate-, and antimicrobial nitroso-derivatives of $InsP_6$. Thus, the present invention exploits the reliance of the *C. difficile* toxins on $InsP_6$ as a virulence factor to develop inositol phosphate based-therapy for CDI.

Figures 3A, 3B, 3C, 3D:
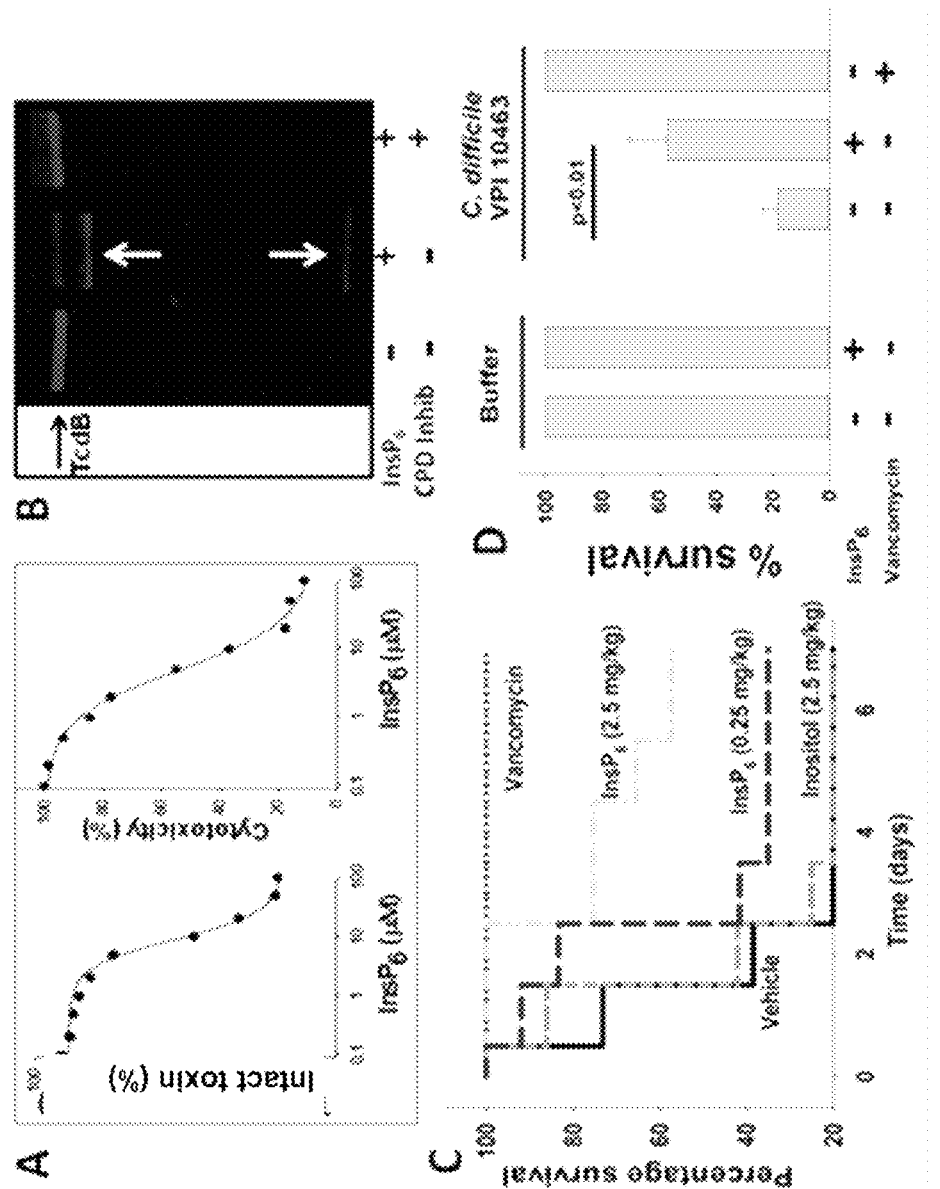

Optimization of Phytase-Resistant $InsP_6$ Analogues for CDI Therapy. Aspects of the present invention provide compositions and methods of neutralizing *C. difficile* exotoxins in the extracellular gut environment. *C. difficile* toxins are autocleaved by $InsP_6$ in the μM range ($IC_{50}$=10 μM; FIGS. 3A-3B). When this autocleavage occurs outside of the cell (by means of $InsP_6$ supplementation), this renders the toxin inactive as the effector domain does not enter the cytosol. The present invention demonstrates that oral $InsP_6$ supplementation is protective in a murine CDI model that closely resembles the human disease. C57BL/6 mice were administered antibiotics and then orally inoculated with $10^4$-to-$10^6$ *C. difficile* (strain VPI 10463). Disease outcome measures included evidence of inflammation and fluid secretion in the caecum and colon of severely afflicted animals, and of characteristic pseudomembraneous histopathologic lesions in the colonic mucosa. Surviving mice developed diarrhea for 5 days post infection and weight loss lasted for 3 to 4 days. Mice continued to shed *C. difficile* bacteria in the stool for up to 13 days post challenge, at which time the experiments were terminated. The highest bacterial dose ($10^6$ CFU) was used to test for $InsP_6$ efficacy given intra-gastrically (0.25-to-2.5 mg/kg/day; range is within the recommended oral daily dose for humans (1,020 mg/day)). These studies demonstrated dose-dependent protective effects of $InsP_6$ that were not evident with inactive myo-inositol (FIGS. 3C-3D).

Phytases are gut-associated acid phosphatases that degrade dietary $InsP_6$ into myo-inositol and inorganic phosphorous. Toxin models indicate that the highly conserved $InsP_6$ binding pocket is readily accessible to inhibitors. The present invention provides an analysis of the allosteric site, tests new small molecule derivatives for toxin cleavage activity, and designs—pharmacophores for use in developing novel phytase-resistant $InsP_6$ derivatives that will not degrade in the intestine. The present invention discloses structural predictions of chemical modifications that optimize toxin cleavage activity for the synthesis of therapeutic $InsP_6$ analogs. This involves targeted synthesis of P1/3 modifications, followed by targeted polymodifications, and finally combinatorial mono-modifications.

Modeling of the Toxin Allosteric Binding Site. As described above, the present invention used homology modeling and MD simulations to determine the likely structure of the CPD in the absence of allosteric $InsP_6$. The flexible β-flap must move to open the $InsP_6$ binding site and block access to the 1a protease active site in the $InsP_6$ free toxin. Thus, a series of conformations are chosen from the molecular dynamics-simulations that reflect different degrees of opening and solvent exposure of the β-flap. A series of $InsP_6$-derivatives are then docked to these conformations, and select the conformation that is most consistent with the experimentally derived activities of these compounds. This conformation is then used for designing 3D-pharmacophores.

To demonstrate feasibility, $InsP_6$ (12 rotatable bonds) was docked to a conformer of TcdA. Of 2aa Autodock poses for $InsP_6$ binding to the open β-flap (inactive) TcdA conformation, 139 clustered together at the lowest binding energy. Their position was confirmed as the $InsP_6$ binding site in the TcdA crystal structure. Probably due to the symmetry of the molecule, the $InsP_6$ in the docking positions was rotated by 60° clockwise about the ring axis and tilted about 50°.

Designing 3D-Pharmacophores Specific for the *C. Difficile* Toxins. Design begins with analysis of the toxin homology models and the bound conformation of $InsP_6$ and the analogs of known activity. A 3D-pharmacophore based on the crystal structure of the bound $InsP_6$ is designed that can be used to optimize the design of phytase-stable $InsP_6$ derivatives. In addition, structure activity relationship analysis of $InsP_6$ derivatives are used with activities determined in toxin cleavage and binding assays. Alternative conformations of the modeled $InsP_6$ binding site, taken from the molecular dynamics simulations, may be used in the structure activity relationship to refine the binding model. Structurally related compounds from the ZINC database in toxin autocleavage assays are examined. Preliminary studies have demonstrated that the inositolhexakissulfate ($InS_6$) analog is an active compound, as are $InsP_7$ derivatives. Of interest, $InsP_7$ derivatives demonstrate enhanced toxin cleavage activity vs. $InsP_6$, indicating that autocleavage efficacy can be achieved in the $IC_{50}$ nM range by optimizing the design for synthesis of the phytase-resistant inositol phosphate derivatives.

Figure 4A:
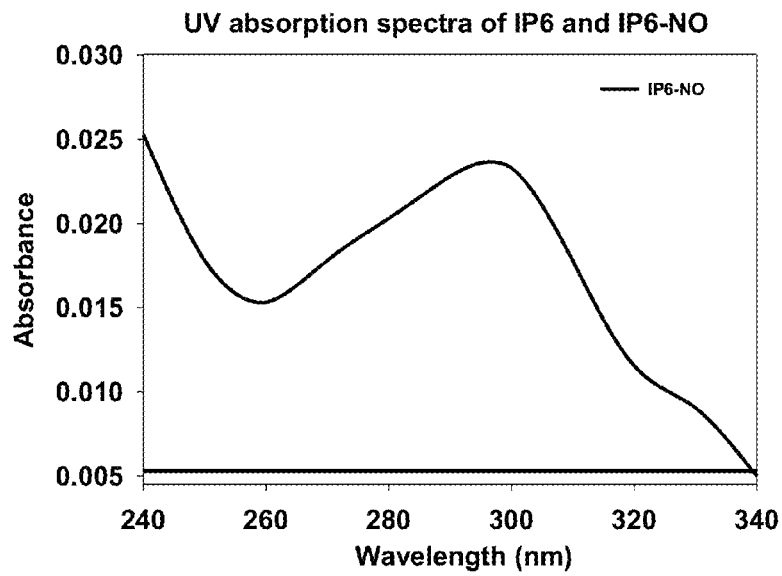

Development of Antimicrobial Nitroso $InsP_6$ Derivatives for CDI Therapy. As described above, stable phytase-resistant $InsP_6$ derivatives that inactive the *C. difficile* toxins are synthesized. As described below, combinatorial antimicrobial activity can be imparted to these derivatives. Because *C. difficile* is highly susceptible to nitric oxide (NO) signals and this has been suggested as an antimicrobial strategy for CDI, NO-derivatives of $InsP_6$ that exert both antimicrobial and antitoxin activity were generated. A 5 molar excess of ethylnitrite was added to $InsP_6$ and incubated at room temperature in the dark for three days. The reaction mixture was dried to completion under nitrogen gas. Dried nitroso-$InsP_6$ was dissolved in water and a UV spectrum analysis was performed. Equilibrium geometries at global minimum energy were calculated using Spartan '08 for windows (See URL wavefun.com on the world wide web), density functional theory (DFT, 6-31G*) level in vacuum phase. The experimental UV spectrum for nitroso-$InsP_6$ is in close agreement with the predicted spectrum for mono-nitrosylated InsP$_6$ with a λ-max at 300 nm (FIG. 4A). Further, calculated energies of InsP$_6$ and InsP$_6$-NO (18.4 kcal/mole) suggested similar stability. Aqueous nitroso-InsP$_6$ was stable at ambient temperature over a period of two weeks.

Figure 4B:
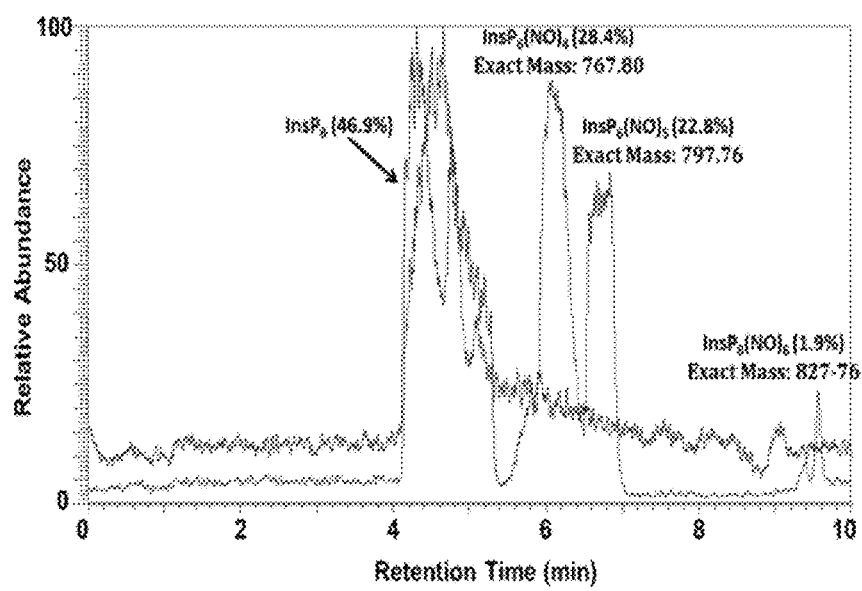
Figure 5A:
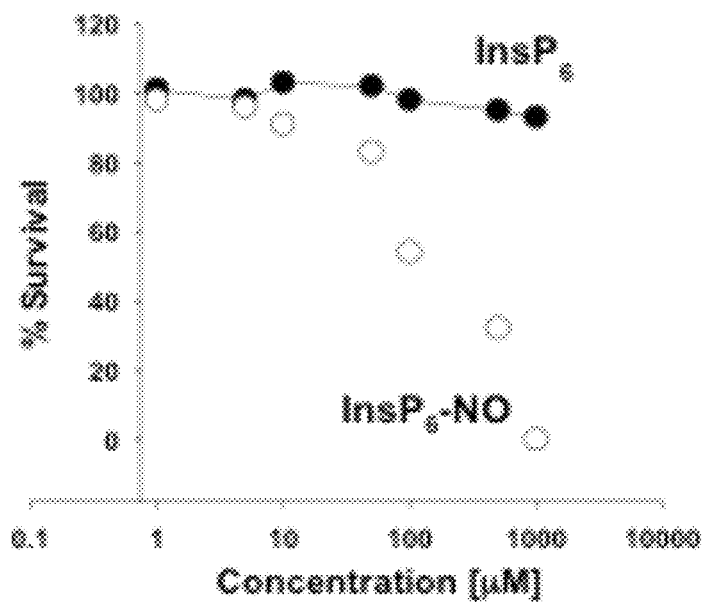
Figure 5B:
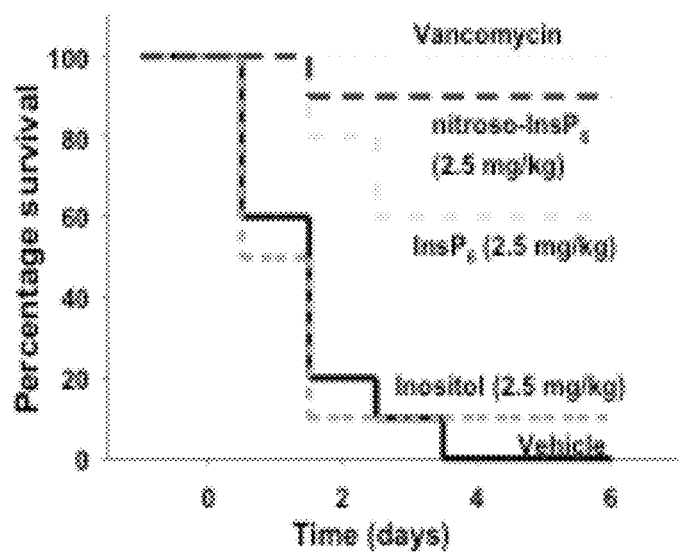
Figure 6:
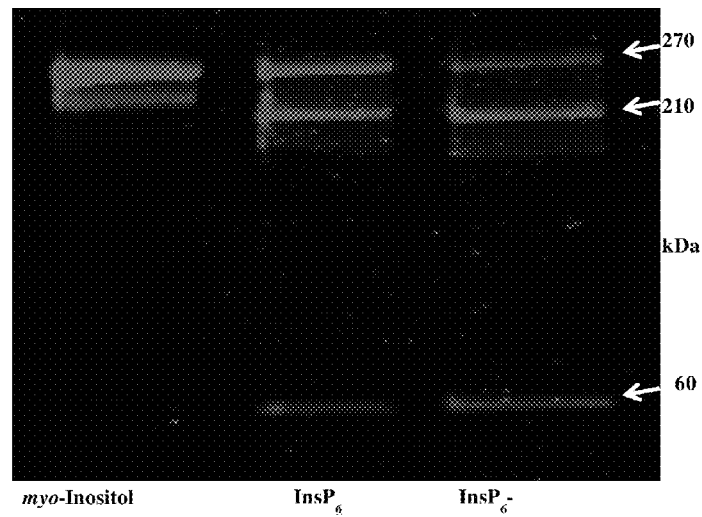
FIG. 6 shows TcdB autocleavage in the presence of 10 µM InsP$_6$ derivatives.

LC-MS was used to separate InsP$_6$ and nitroso-InsP$_6$ derivatives. The mass spectrum showed four peaks. The first peak matched the InsP$_6$ standard, and later peaks showed a mass spectrum that corresponded to a mixture of nitroso-InsP$_6$(NO)$_{4-6}$ derivatives, with approximate yields ranging from 2-28% (FIG. 4B). Further, the nitroso-InsP$_6$ derivatives demonstrated significant antimicrobial activity towards C. difficile and showed enhanced disease amelioration in experimental CDI (FIGS. 5A-5B), without altering toxin cleavage efficiency (FIG. 6).

Characterization and Preparation of Optimal Nitroso InsP$_6$ Derivatives. The LC conditions are refined to separate out the different NO-derivatives in sufficient quantities of pure material so as to test them individually in antimicrobial and toxin assays, and phytase-enzymatic assays. MS is used to determine the size of each adduct, and as an approximate indicator of purity. With a reasonably pure, active molecule, the structure can be determined in more detail, using a combination of $^{31}$P- and Proton NMR. Initially, these studies determine whether the NO is covalently linked or remains as a free radical adduct. In the latter case, the distinctive proton resonances for the hydrogens should allow one to discriminate which position on the InsP$_6$ has been modified. If the bond is indeed covalent, the synthesis is repeated, incorporating $^{15}$NO. In an effort to isolate and quantify nitroso-InsP$_6$, a Q-Trap 2000 (Hybrid MS) is used, combination of trap [identification of unknown InsP$_6$-(NO)$_X$ by mass spectral fragmentation] and triplequad mass spectrometry. Finally, synthesis conditions (variations in time, temperature, molar excess of ethylnitrite and other NO donors) are optimized to increase the yield of the various active nitroso-InsP$_6$ derivatives.

Figure 7:
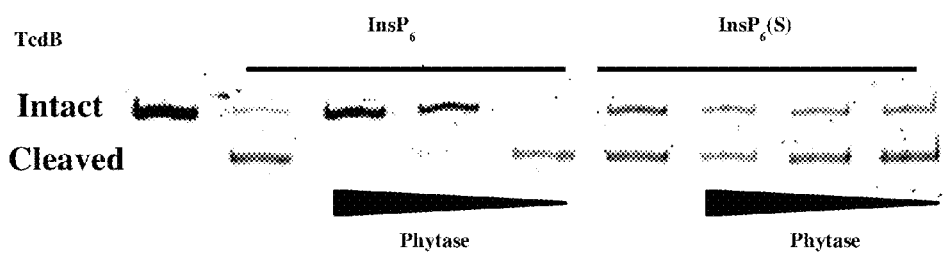
FIG. 7 shows an increased phytase resistance of myo-inositol-hexaphosphorothioate (InsP6(S)).

In Vitro Testing of Nitroso-InsP$_6$ Derivatives. In vitro testing and measurement of binding affinities of compounds are performed using toxin cleavage assays, and by radioligand or BIACORE-toxin binding studies, respectively. For medium throughput toxin cleavage assays, autocleavage of 1 µg TcdA and TcdB holotoxins is performed in 25 µL 20 mM Tris-HCl, 150 mM NaCl (pH 7.4) with and without InsP$_6$ for 10-60 min at 37° C. (FIG. 6). Cleavage reactions are then stopped with SDS-PAGE loading buffer and boiling at 96° C. for 5 min. Samples are then run under reducing conditions on 4-20% gradient gels and cleavage products stained with Gelcode-Biue™ for 1 hr and cleared in water overnight. AC$_{50}$ and IC$_{50}$ concentrations are calculated by measuring the relative absorbance of cleavage fragments relative to intact toxin using a LiCor Odyssey infrared scanner (λ=680 nm). Cleavage is plotted against ligand concentration using four-parameter logistic curve fitting on SigmaPlot 11.0 software. If the toxin cleavage efficiency remains unaltered in purified nitroso-InsP$_6$ fractions, then toxin Rac1 glucosylation and cell rounding assays are initiated to evaluate cytoprotection in cell culture systems. Antimicrobial activity is then recorded as shown in FIGS. 5A-5B. Finally, if a covalent modification is formed with NO, it is contemplated that this shows phytase-resistance. Thus, enzymatic digestions of nitroso-InsP$_6$ derivatives are carried out with EC 3.1.3.8 (type 3 phytase); EC 3.1.3.72 (type 5 phytase), and EC 3.1.3.26 (type 4/6 phytase) to test whether the NO-modifications are nonhydrolysable (e.g., FIG. 7).

TABLE 1

Representative AC$_{50}$ (concentration that provides half the maximum activity) for representative inositol analogs.

| Compound | | AC50 (µM) |
|---|---|---|
| myo-inositol-(1,3,4,5-tetrakisphosphate) | Myo-InsP4(2,6) | >1000 |
| myo-inositol-(1,2,3,5-tetrakisphosphate) | Myo-InsP4(4,6) | >1000 |
| myo-inositol-(2,3,4,5,6-pentakisphosphate) | Myo-InsP5(1) | 8.67 |
| myo-inositol-(1,3,4,5,6-pentakisphosphate) | Myo-InsP5(2) | 10.47 |
| myo-inositol-(1,2,4,5,6-pentakisphosphate) | Myo-InsP5(3) | 95.56 |
| myo-inositol-(1,2,3,5,6-pentakisphosphate) | Myo-InsP5(4) | >1000 |
| myo-inositol-hexakisphosphate | Myo-InsP6 | 14.79 |
| myo-inositol-(1,2,3,4,5,6-phosphorothioate) | Myo-InsP6(S) | 1.99 |
| (1/3)-phospho-myo-inositol hexaakisphosphate | Myo-InsP7(1/3) | 3.04 |

It is proposed that an NO adduct is capable of forming with InsP$_6$ which confers antimicrobial activity towards C. difficile (without significantly altering the toxin autocleavage efficiency). Studies in an experimental CDI model demonstrate that intra-colonic targeting of nitroso-InsP$_6$ enhances the efficacy of InsP$_6$ to 90% survival rates following administration of the antimicrobial derivatives. Because of the current uncertainty of the nitroso-InsP$_6$ chemistry, there may be potential limitations to oral nitroso-InsP$_6$ delivery as this molecule may show poor colonic bioavailability due to degradation and absorption in the small intestine.

Any patents or publications mentioned in this specification are indicative of the levels of those skilled in the art to which the invention pertains. Further, these patents and publications are incorporated by reference herein to the same extent as if each individual publication was specifically and individually incorporated by reference.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention.

The invention claimed is:

1. A method for neutralizing a Clostridium difficile bacterial toxin, comprising contacting the C. difficile bacterial toxin with an inositol hexakisphosphate analog having a chemical structure of Formula I:

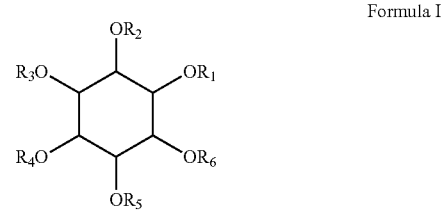

Formula I wherein R$_1$, R$_2$, R$_3$, R$_4$, R$_5$, and R$_6$ are —PS(OH)$_2$.

2. The method of claim 1, wherein the *Clostridium difficile* bacterial toxin is TcdA, TcdB, or TcdA and TcdB.

3. The method of claim 1, wherein the *C. difficile* bacterial toxin is in a subject having a *Clostridium difficile* infection.

4. The method of claim 3, wherein the analog is administered orally to the subject.

5. The method of claim 1, wherein nitric oxide (NO) is bound to at least one of $R_1$, $R_2$, $R_3$, $R_4$, $R_5$, and $R_6$.

* * * * *